United States Patent
Yokoyama et al.

(10) Patent No.: US 6,240,202 B1
(45) Date of Patent: May 29, 2001

(54) APPEARANCE INSPECTION METHOD FOR ELECTRONIC PARTS

(75) Inventors: Haruhiko Yokoyama, Osaka; Masatoshi Nakamura, Nishinomiya, both of (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/125,341

(22) PCT Filed: Feb. 26, 1997

(86) PCT No.: PCT/JP97/00540

§ 371 Date: Aug. 14, 1998

§ 102(e) Date: Aug. 14, 1998

(87) PCT Pub. No.: WO97/32183

PCT Pub. Date: Sep. 4, 1997

(30) Foreign Application Priority Data

Feb. 27, 1996 (JP) .................................................. 8-039764

(51) Int. Cl.$^7$ .................................. G06K 9/48; G06K 9/56
(52) U.S. Cl. ......................... 382/149; 382/203; 382/289; 382/151
(58) Field of Search .................................... 382/108, 141, 382/145, 146, 149, 151, 199, 205, 266, 272, 276, 286, 308, 289, 203; 250/559.22, 559.34, 559.37, 559.41, 559.39, 559.45; 348/87, 92, 125, 126, 128; 356/376, 237.3, 237.4, 237.5; 702/40, 82, 151, 159, 167; 708/6, 443

(56) References Cited

U.S. PATENT DOCUMENTS

| | | | |
|---|---|---|---|
| 4,695,884 | * | 9/1987 | Anastassiou et al. ................ 358/163 |
| 4,974,261 | * | 11/1990 | Nakahara et al. ...................... 382/22 |
| 5,185,812 | * | 2/1993 | Yamashita et al. ....................... 382/8 |
| 5,434,802 | * | 7/1995 | Matsumoto ........................... 364/559 |
| 5,627,912 | * | 5/1997 | Matsumoto ........................... 382/146 |

FOREIGN PATENT DOCUMENTS

| | | |
|---|---|---|
| 412209 | 1/1992 | (JP) . |
| 450713 | 2/1992 | (JP) . |
| 5166904 | 7/1993 | (JP) . |

* cited by examiner

*Primary Examiner*—Leo Boudreau
*Assistant Examiner*—Brian P. Werner
(74) *Attorney, Agent, or Firm*—Price and Gess

(57) ABSTRACT

An external appearance inspection method for electronic components for detecting the presence of unevenness in the outline thereof. An approximately square-shaped outline (1) of an electronic component under inspection is extracted, this outline (1) is differentiated, and the presence of unevenness in the outline (1) is determined according to the absolute value of the difference between the maximum and minimum values (10, 11) of the differential values and the median (12) thereof.

10 Claims, 4 Drawing Sheets

Fig. 9 *PRIOR ART*
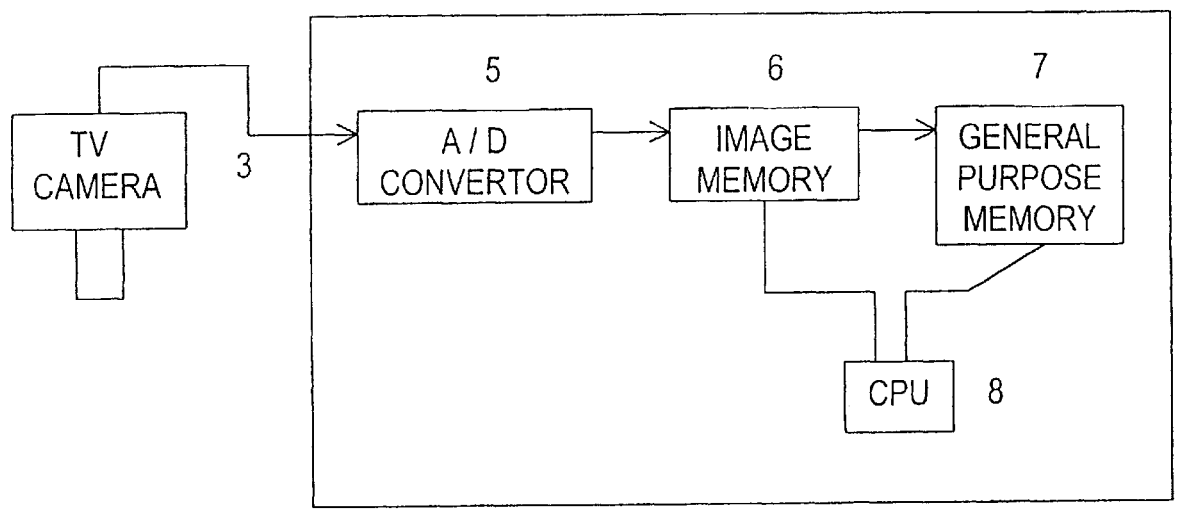
Fig. 10
*PRIOR ART*
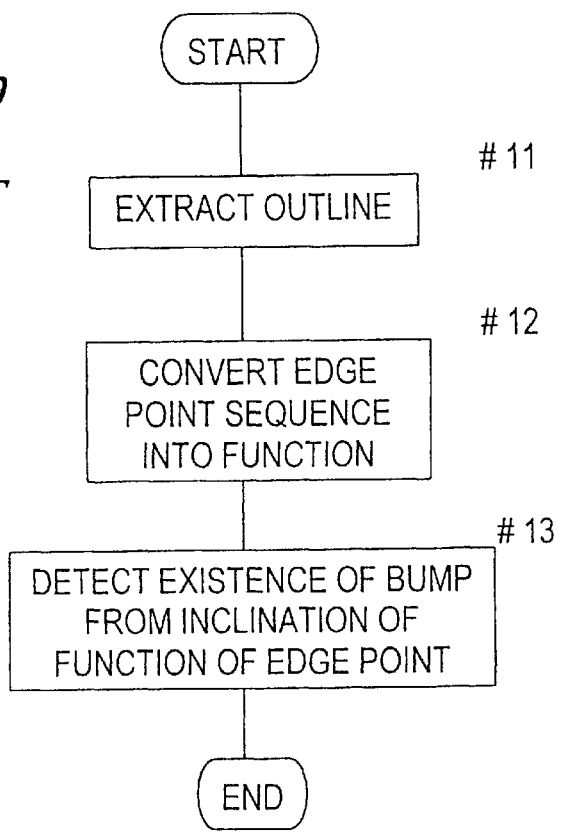

APPEARANCE INSPECTION METHOD FOR ELECTRONIC PARTS

DESCRIPTION

RELATED APPLICATION

This application claims priority pursuant to 35 U.S.C. §371 from PCT/JP97/00540, with an International Filing Date of Feb. 26, 1997 and a priority date of Feb. 27, 1996, from Japanese Application No. 8-39764.

1. Technical Field

The present invention relates to an external appearance inspection method for electronic components for detecting unevenness in the outline of electronic components.

2. Background Art

Inspection of electronic components such as capacitors and the like includes inspection for detecting unevenness of various types in external surfaces, especially unevenness known as bumps, flash, or the like (hereafter, simply called "bumps" in the present description). Bumps can occur in any position, but by using a plurality of cameras, or by taking images in a plurality of directions using a single camera, all bumps can be detected as unevenness in the outline of the component. In particular, it is possible to detect unevenness in the component outline by positioning a camera such that its optical axis lies in a direction wherein a portion having a high incidence of bumps can be detected as an outline.

A conventional external appearance inspection method for detecting bumps in electronic components as unevenness in the component outline is now described with reference to FIG. 8–FIG. 10.

FIG. 8 shows an image of a capacitor which is the subject of inspection. The reference numeral 1 denotes the outline of the capacitor, 2 indicates a bump region, and θ is the angle of the bump.

FIG. 9 shows the construction of an external appearance inspection apparatus. The reference numeral 3 is a video camera, and 4 is a data processing unit, which comprises an A/D converter 5 for analogue image signals transmitted from the video camera 3, an image memory 6 for digital image signals, a general-purpose memory 7, and a CPU 8 (data processing unit). The general-purpose memory 7 stores outlines, outline differential values, outline angles, and the like, extracted from the image signal.

Next, the data processing implemented by the CPU 8 in order to inspect bumps is described with reference to FIG. 10. An image of a capacitor, which is the component under inspection, is previously taken by the video camera 3, and this image signal is A/D converted and stored in the image memory 6. Thereupon, the image is scanned successively in one direction and the points at which the density change is greatest are extracted as outline points (step #11). The series of edge points are then corrected into a function to obtain an outline (step #12). Thereupon, the gradient of the function of the edge point series is determined. Here, if there is a bump, the gradient will increase (gradient with respect to horizontal axis; angle θ), so a uniform gradient is previously determined as a reference value, and if there is an absolute value greater than this reference value, it is determined that there is a bump (step #13). Bumps are detected on the lower edge, right-hand edge and left-hand edge by means of the same approach. In the case of the right-hand and left-hand edges, a gradient angle with respect to the vertical axis is used.

However, in the conventional method described above, if the capacitor is in an inclined position, there is a risk that the gradient will rise and a bump will be detected even in regions where there is no bump, thereby yielding inaccurate inspection results and leading to poor reliability.

In view of the aforementioned problems of the prior art, it is an object of the present invention to provide a highly reliable external appearance inspection method for electronic components, whereby the presence of unevenness in a component outline can always be detected accurately.

DISCLOSURE OF INVENTION

The external appearance inspection method according to the present invention comprises the steps of: extracting an approximately square-shaped outline of an electronic component under inspection; differentiating the outline; extracting a median from series of differential values; detecting maximum and minimum values in the differential values; and determining unevenness in the outline according to an absolute value of the difference between the maximum and minimum values of the differential values and the median thereof; and it enables unevenness in the outline to be detected in a stable manner, without detrimental effects due to inclination of the object under inspection.

BRIEF DESCRIPTION OF DRAWINGS

FIG. 9 is a block diagram showing the construction of a conventional external appearance inspection device; and FIG. 10 is a flowchart of a conventional external appearance inspection method.

BEST MODES FOR CARRYING OUT THE INVENTION

A preferred embodiment of the present invention is described below with reference to FIG. 1–FIG. 7. The shape of the capacitor, which is the electronic component under inspection, is the same as that in FIG. 8 used in the conventional example. Furthermore, the overall construction of the external appearance inspection device is the same as that in FIG. 9 described in relation to the conventional example, and the description thereof is referred to here.

Figure 1:
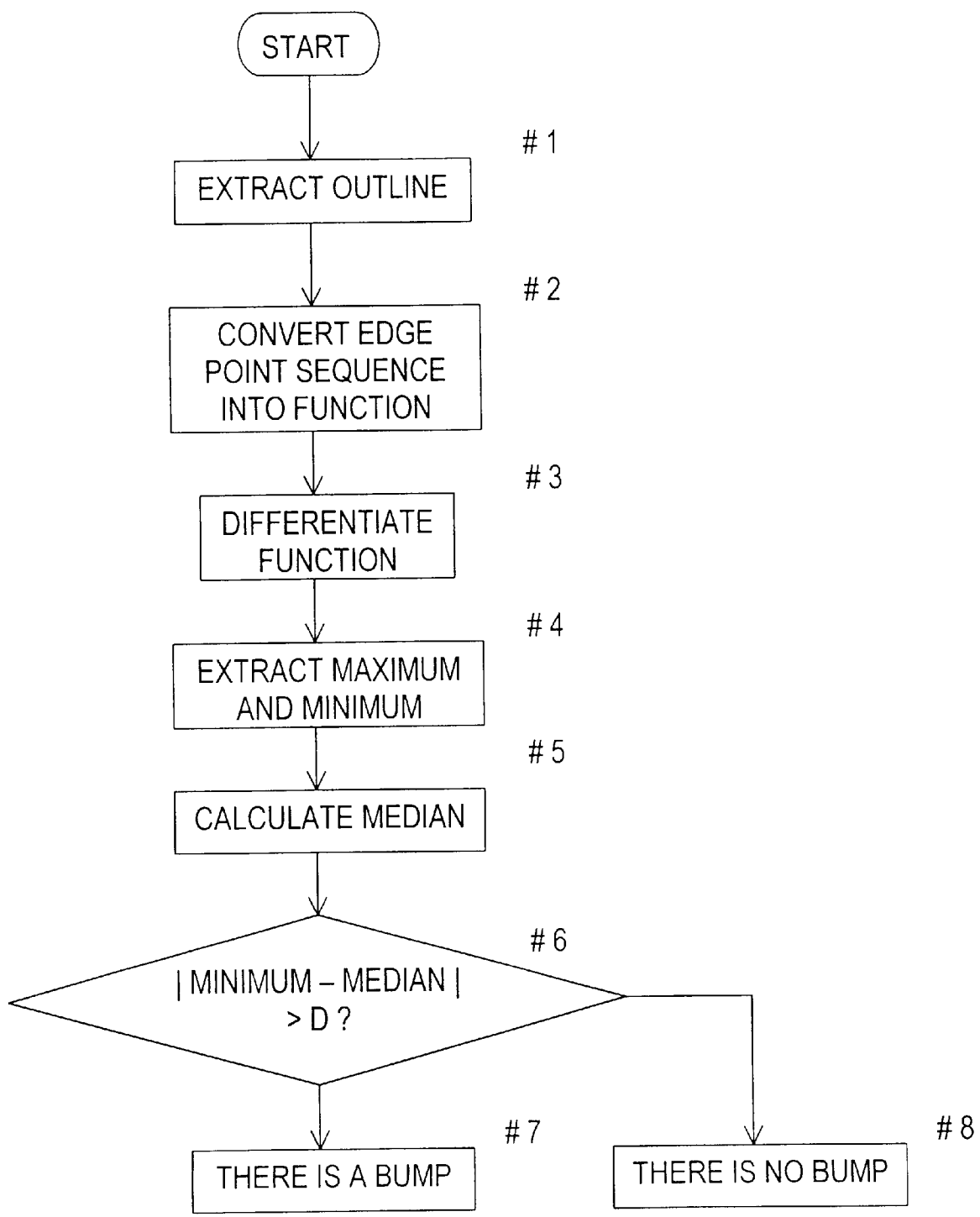
FIG. 1 is a flowchart of an external appearance inspection method according to one embodiment of the present invention.

A data processing method implemented by the CPU 8 when inspecting bumps in a capacitor according to this embodiment is described with reference to FIG. 1. An image of a capacitor, which is the object under inspection, is previously taken by the video camera 3, and this image signal is A/D converted and stored in the image memory 6.

Figure 2:
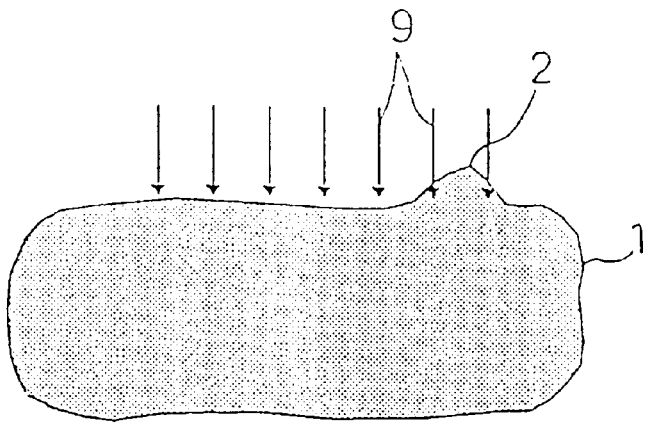
FIG. 2 is a diagram illustrating an image of a capacitor, which is the object under inspection, and the direction of scanning when extracting an outline according to the embodiment.
Figure 3:
FIG. 3 is a diagram illustrating an outline extracted from the image in FIG. 2.
Figure 4:
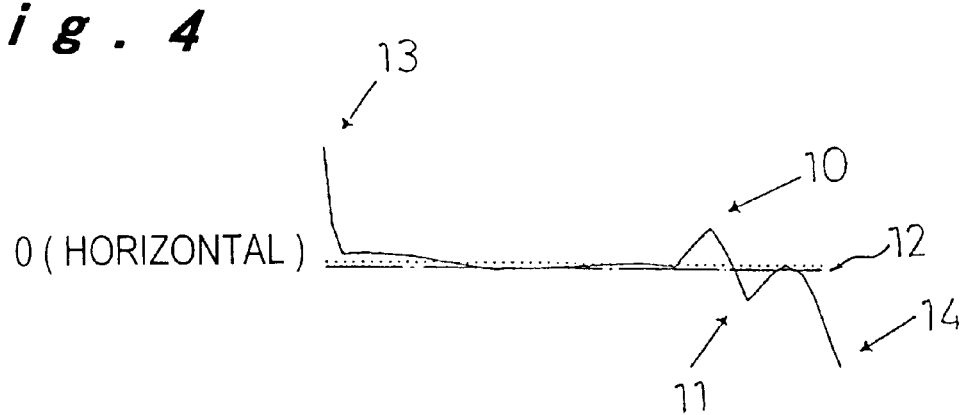
FIG. 4 is a diagram illustrating the differential values for the outline in FIG. 3.

FIG. 2 shows the image stored in the image memory 6. Firstly, the image is scanned in the direction indicated by arrow 9 in FIG. 2, and the points of maximum density change are extracted as outline points (step #1). Thereupon, a function of the outline as shown in FIG. 3 is obtained by converting the edge point series (step #2). Next, the differential values thereof are calculated from the outline function, as shown in FIG. 4 (step #3).

The concrete method of differentiation is as follows. The operator (−1, +1) is used as an example. In the case of using this operator, the differential value $\Delta a_i$ can be obtained with respect to the co-ordinates series of the outline, $\{a_i\}$, by the formula $$\Delta a_i = a_{i+1} - a_i.$$

Moreover, it is advantageous if an operator which involves smoothing is used as the aforementioned operator. Specifically, an operator such as $$(-1,1)*(1,1)^2 = (-1,+1)*(1,3,3,1) = (1, 2, 0, -2, -1)$$

can be used. By using such operator, apparent edges of sampling can be smoothed, which is sometimes better than a (−1, +1) operator in the case of smooth surface in, for instance, a component formed by sintering, such as capacitors or the like.

After differentiation, in this way, the maximum, minimum and medians are found (steps #4, #5). In FIG. 4, the reference numeral 10 is a maximum value, 11 is a minimum value, 12 is a median, 13 is an absolute maximum and 14 is an absolute minimum. The maximum values are larger than the differential values on either side thereof by a certain prescribed value or more, and the minimum values are less than the differential values on either side thereof by a certain prescribed value of more, and they differ from the absolute maximum and absolute minimum, respectively. The median 12 is the centrally placed value when all the differential values are lined up in order of magnitude. In the example in FIG. 4, the median takes a value in the proximity of zero (horizontal axis).

Next, after finding the aforementioned maximum value, minimum value and the median, |maximum value−median| and |minimum value−median| are compared respectively with the reference value (indicating the gradient of a bump) (step #6), and if one of these is larger than the reference value, it is considered that there is a bump (step #7), whilst if these values are less than the reference value, it is considered that there is no bump (step #8). Maximum and minimum values are used because if simply the largest and smallest values are used, places where the gradient increases at the corners of the capacitor may be detected mistakenly as bumps, whereas if maximum and minimum values are used, bumps can be detected accurately.

Figure 5:
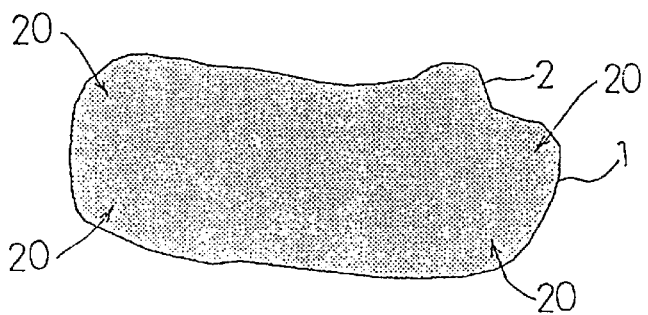
FIG. 5 is a diagram showing an image of a capacitor which is in an inclined position in the embodiment.
Figure 6:
FIG. 6 is a diagram illustrating an outline extracted from the image in FIG. 5.
Figure 7:
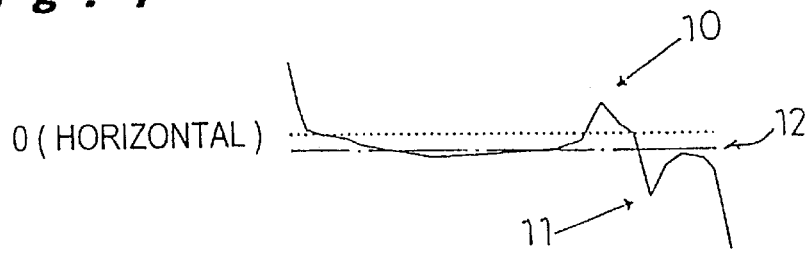
FIG. 7 is a diagram illustrating the differential values for the outline in FIG. 6.
Figure 8:
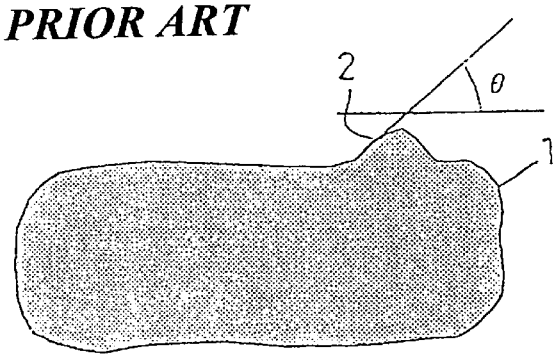
FIG. 8 is a diagram showing an image of a capacitor, which is the object under inspection.

Furthermore, the advantages of using a median are as follows. FIG. 5 shows a capacitor which is in an inclined position. FIG. 6 shows the function of outline points detected from this outline, and FIG. 7 shows differential values for these points. Since the capacitor is inclined, the differential values are shifted downwards for the whole component (in the example shown, the capacitor is inclined downwards to the right, so the differential values are shifted downwards, but if it was inclined upwards to the right, they would be shifted upwards.) The median 12 takes a value shifted to the minus side of zero (horizontal axis) by an amount corresponding to the gradient of the capacitor, and in the aforementioned formula, the inclination of the capacitor is corrected by taking the difference with respect to this median.

The median used is the value which is centrally placed when all the differential values are arranged in order of magnitude, but if the average value of all the differential values is used, the result will be affected significantly by portions at the corners 20 of the capacitor where the differential value is extremely large, and therefore the inclination will not be reflected accurately. By arranging the differential values in order, the large values are ignored and there is no effect due to the corner region 20.

Furthermore, it is also possible to check whether the inclination derived in this way is accurate by comparing the inclination of the upper, lower, right-hand and left-hand edges (these should be at 90° intervals). An average of the four edges may be finally used, or, if one edge of the component only is significantly out of place, values for the three other edges or the average thereof may be used.

INDUSTRIAL APPLICABILITY

As set forth above, according to the external appearance inspection method for electronic components of the present invention, since an approximately square-shaped outline of an electronic component under inspection is extracted, this outline is differentiated, and unevenness in the outline is determined according to an absolute value of the difference between maximum and minimum values of the differential values and the median thereof, it is possible to detect unevenness in the outline reliably without detrimental effects due to inclination of the object under inspection, thereby providing a useful external appearance inspection method for electronic components such as capacitors.

What is claimed is:

1. An external inspection method for electronic components comprising the steps of:

extracting an outline function representative of a surface contour of an electronic component;

differentiating the outline function to provide a series of differential values;

extracting a median from the series of differential values;

detecting maximum and minimum values in the differential values; and determining the presence of unevenness in the surface contour of the electronic component by calculating an absolute value of the difference between the maximum and the median values, and calculating an absolute value of the difference between the minimum and the median values and comparing the differences to a predetermined value.

2. A method for determining the acceptability of an electronic component by evaluating its external appearance, comprising the steps of:

imaging the electronic component to provide a plurality of outline values representative of a scan of the electronic component;

extracting an outline function for each side of the electronic component to provide a representation of a surface perimeter about an entire body of the electronic component from the outline values;

differentiating the outline functions;

extracting maximum and minimum values and median values from the differentiation; and determining the presence of unevenness in the surface contour of the electronic component by calculating an absolute value of the difference between the maximum and the median values, and calculating an absolute value of the difference between the minimum and the median values and comparing the differences to a predetermined value.

3. The method of claim 2, further including the step of comparing an inclination of respective side edges of the electronic component.

4. The method of claim 2, wherein an operator is used for differentiation, which can smooth the outline values.

5. A method for determining the acceptability of an electronic component by evaluating its external appearance, comprising the steps of:

imaging the electronic component to provide a plurality of outline values representative of a scan of the surface of the electronic component;

extracting an outline function representative of at least a portion of a surface perimeter of a body portion of the electronic component from the outline values;

differentiating the outline surface function;

extracting maximum and minimum values of the surface portion from the differentiation;

determining a median value; and determining the presence of unevenness in the surface contour of the electronic component by calculating an absolute value of the difference between the maximum and the median values, and calculating an absolute value of the difference between the minimum and the median values and comparing the differences to a predetermined value.

6. The method of claim 5 wherein differentiating is performed with an operator that provides a surface smoothing to remove small irregularities.

7. The method of claim 5 wherein the median is determined by arranging the differential values in order of magnitude and disregarding large values representative of corners of the electronic component.

8. The method of claim 7 wherein differentiating is performed with an operator that provides a surface smoothing to remove small irregularities.

9. The method of claim 5 wherein the steps are repeated for each side of the electronic component to provide a surface perimeter and a further step of verifying by comparing the inclination of each side relative to adjacent sides to determine if a 90° angle is formed.

10. The method of claim 9 wherein the outline function represents an approximately 90° cornered outline having four corners.

* * * * *